US00PP33354P2

(12) United States Plant Patent
Quisenberry et al.

(10) Patent No.: US PP33,354 P2
(45) Date of Patent: Aug. 17, 2021

(54) PLUM TREE NAMED 'BLACKRED X'

(50) Latin Name: *Prunus salicina*
Varietal Denomination: BLACKRED X

(71) Applicants: Jon M. Quisenberry, Le Grand, CA (US); Lowell Glen Bradford, Le Grand, CA (US)

(72) Inventors: Jon M. Quisenberry, Le Grand, CA (US); Lowell Glen Bradford, Le Grand, CA (US)

( * ) Notice: Subject to any disclaimer, the term of this patent is extended or adjusted under 35 U.S.C. 154(b) by 0 days.

(21) Appl. No.: 16/974,337

(22) Filed: Jan. 4, 2021

(51) Int. Cl.
*A01H 5/08* (2018.01)
*A01H 6/74* (2018.01)

(52) U.S. Cl.
USPC ..... Plt./184

(58) Field of Classification Search
USPC ..... Plt./156, 184
See application file for complete search history.

(56) References Cited

U.S. PATENT DOCUMENTS

PP19,576 P2 12/2008 Bradford
PP20,832 P2 3/2010 Bradford

*Primary Examiner* — Susan McCormick Ewoldt
*Assistant Examiner* — Karen M Redden

(57) ABSTRACT

The present invention relates to a plum tree, *Prunus salicina*, and more particularly to a new and distinct variety broadly characterized by a small to medium size, moderately vigorous, hardy, and productive tree. Being self-unfruitful, the present variety requires cross pollination from an apricot, interspecific, or plum that blooms during the mid to late season, such as 'Blackred IV' interspecific tree (U.S. Plant Pat. No. 20,832). The present variety produces a heavy amount of flowers that produce a moderate amount of pollen to entice good bee activity to facilitate pollination. The fruit matures under the ecological conditions described during late June, with first picking on Jun. 29, 2020. The fruit is uniformly medium in size, very dark purplish red in skin color, very dark red in flesh color, semi-freestone in type, globose in shape, firm in texture, juicy, very sweet, and very good in flavor.

1 Drawing Sheet

Botanical classification: *Prunus salicina.*
Varietal denomination: 'BLACKRED X'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree which has been denominated varietally as 'BLACKRED X'.

During a typical blooming season we isolate as seed parents both individual and groups of different plum and interspecific trees by covering them with screen houses. A hive of bees is placed inside each such house, and bouquets to provide pollen from different plum, apricot, and interspecific hybrid trees are placed in buckets near the trees approximately every two days for the duration of the bloom. During 2008 one such house containing 'Blackred V' interspecific tree (U.S. Plant Pat. No. 19,576) was crossed by us in this manner. To pollinate this interspecific tree, we selected bouquets from several sources of plum trees without keeping specific written details. Upon reaching maturity the fruit from this interspecific tree was harvested, and the seeds were removed, cracked, stratified and germinated as a group with the label "H41". They were grown as seedlings on their own root in our greenhouse and upon reaching dormancy transplanted to a cultivated area of our experimental orchard located near Le Grand, Calif. in Merced County (San Joaquin Valley). During the summer of 2012 the claimed variety was selected by us as a single plant from the group of seedlings described above. Subsequent to origination of the present variety of plum tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is most similar to its seed parent 'Blackred V' interspecific tree (U.S. Plant Pat. No. 19,576), by being self-unfruitful and by producing fruit that matures in late June and that is fairly globose in shape, firm in texture, juicy, very sweet, and very good in flavor, but is distinguished therefrom by producing fruit that is somewhat darker red in flesh color, dark purplish red instead of genetically black in skin color, larger in size, semi-freestone instead of clingstone in type, and more tolerant to high temperatures during the harvest season.

SUMMARY OF VARIETY

The present plum variety is characterized by a small to medium size, moderately vigorous, hardy, and productive tree. Being self-unfruitful, the present variety requires cross pollination from an apricot, interspecific, or plum that blooms during the mid to late season, such as 'Blackred IV' interspecific tree (U.S. Plant Pat. No. 20,832). The present variety produces a heavy amount of flowers that produce a moderate amount of pollen to entice good bee activity to facilitate pollination. The fruit matures under the ecological conditions described during late June, with first picking on Jun. 29, 2020. The fruit is uniformly medium in size, very dark purplish red in skin color, very dark red in flesh color, semi-freestone in type, globose in shape, firm in texture, juicy, very sweet, and very good in flavor.

DRAWING

The accompanying photograph consists of four whole fruits positioned to display the characteristics of the skin color and form, one divided fruit to reveal the flesh and stone, a tip shoot growth, typical leaves, and three insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif. The fruit description was developed at the state of full ripe on Jul. 15, 2020, on the original tree during its tenth growing season. The flower and bud descriptions were developed during the previous blooming season. All major color code designations are by reference to the Inter-Society Color Council, National Bureau of Standards. Common color names are also used occasionally.

PARENTAGE

Seed parent: Blackred V (U.S. Plant Pat. No. 19,576) interspecific tree.

Pollen parent: Unknown plum.

TREE

Size: Medium to small, reaching and maintaining a height of 8' [2.44 m.] and a spread of 6' [1.83 m.] after ten growing seasons utilizing typical dormant pruning.

Vigor: Moderately vigorous, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Central leader.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-unfruitful, requiring cross pollination by a suitable mid seasonal blooming apricot, interspecific, or plum, such as 'Blackred IV' interspecific tree (U.S. Plant Pat. No. 20,832).

Bearing: Regular bearer, weather dependent, no crop failures observed as of yet.

Trunk:

- *Size.*—Medium, reaching a maximum diameter of 3" [76 mm.] after the tenth growing season.
- *Texture.*—Medium to shaggy.
- *Bark color.*—A Moderate brown [58. m.Br] and Deep brown [56. deep Br] variegation with Dark yellowish brown [78. d.yBr] crevices present.
- *Lenticels.*—Approximate Number Per Square Inch: 8. Color: Strong brown [55. s.Br]. Average Size: ¼" [6.4 mm.] in length. The width is typically one fourth as much as the length. Shape: Elongated.

Branches:

- *Size.*—Medium, scaffold diameter is 2½" [63.5 mm.] measured 12" above the first hanger, maximum diameter is 1½" [38.1 mm.] of the first hanger.
- *Texture.*—Medium on first and second year wood, increasing roughness with age.
- *Color.*—1st Year Wood Topside: Grayish red [19. gy.R]. 1st Year Wood Underside: Brilliant yellow green [116. brill.YG]. Older Wood: A Grayish brown [61. gy.Br] and Brownish gray [64. brGy] variegation with Dark grayish brown [62. d.gy.Br] crevices present.
- *Lenticels.*—Number Per Square Inch: About 25 on second year wood. Color: Grayish yellowish brown [80. gy.yBr]. Average Size: Small, 1/32" [0.8 mm.] in length. The width is typically one fourth as much as the length. Shape: Elongated.

Leaves:

- *Size.*—Medium. Average Length: 3¾" [95.3 mm.]. Average Width: 1¾" [44.5 mm.].
- *Arrangement.*—Alternate.
- *Thickness.*—Medium.
- *Form.*—Elliptical.
- *Apex.*—Acuminate.
- *Base.*—Acute with an average base angle of 60 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Petiole.*—Average Length: ¼" [6.4 mm.]. Average Thickness: 1/16" [1.6 mm.]. Color: Pale yellow green [121. p.YG] with some Grayish red [19. gy.R] areas where exposed toward the sun. Stipules. — Number: Mostly 2 per leaf, up to 6 per growing tip. Average Length: ¼" [6.4 mm.]. Color: Pale yellow green [121. p.YG] becoming Dark greenish yellow [103. d.gY] with age.
- *Glands.*—Number: Mostly 2 per leaf. Position: Mostly alternate, positioned at the intersection of the petiole and base of leaf blade. Form: Globose. Size: Small to medium, 1/32" [0.8 mm.] in diameter. Color: Strong yellow green [117. s.YG] becoming Moderate reddish brown [43. m.rBr] in the center with age. Leaf buds: Pointed.

Flower buds:

- *Hardiness.*—Hardy, with respect to central California blooming season.
- *Diameter.*—Typically 3/16" [4.8 mm.] 1 week before bloom.
- *Length.*—Typically ⅜" [9.5 mm.] 1 week before bloom.
- *Form.*—Free, not touching.
- *Surface.*—Slightly pubescent.
- *Tip color.*—White [263. White].

Flowers: Perfect, complete, perigynous, usually a single pistil, about thirty stamens, five sepals and petal locations alternately positioned.

*Average flower diameter.*—1 3/16" [30.2 mm.].
*Average flower depth.*—3/8" [9.5 mm.] when fully open.
*Number of petals.*—Five, no double blossoms observed.
*Petal shape.*—Oval.
*Petal margin.*—Entire, somewhat wavy.
*Petal arrangement.*—Overlapping.
*Average petal diameter.*—9/16" [14.3 mm.].
*Average petal length.*—5/8" [15.9 mm.].
*Petal apex.*—Rounded.
*Petal base.*—Obtuse.
*Petal color.*—White [263. White] on both sides.
*Anther color.*—Brilliant yellow [83. brill.Y].
*Pollen production.*—Moderate, enticing to bees.
*Stigma color.*—Brilliant greenish yellow [98. brill.gY].
*Stigma position.*—Located slightly above the average anther position.
*Stamen position.*—Typically located about 1/32" [0.8 mm] below the petals.
*Sepal color.*—Vivid yellow green [115. v.YG] on the outside, Light yellow green [119. l.YG] on the inside.
*Sepal outer surface.*—Slightly pubescent.
*Sepal length.*—3/16" [4.8 mm.].
*Sepal width.*—1/8" [3.2 mm.].
*Sepal apex.*—Rounded to elliptical to match the width and length.
*Sepal margin.*—Fairly smooth.
*Average pistil length.*—11/16" [17.5 mm.].
*Average stamen length.*—9/16" [14.3 mm.].
*Ovary.*—Smooth.
*Fragrance.*—Moderate.
*Pollen production.*—Moderate, bee enticing.
*Bloom density.*—Heavy.
*Number per cluster.*—2 to 5, mostly 3.
*Blooming period.*—Medium to late, about two days after 'Santa Rosa' plum (unpatented).
*Onset of bloom.*—One percent on Feb. 24, 2020.
*Date of full bloom.*—Mar. 4, 2020.
*Duration of bloom.*—One to two weeks, dependent on ambient temperature.

FRUIT

Maturity when described: Full ripe, Jul. 15, 2020.
Date of first picking: Jun. 29, 2020.
Date of last picking: Jul. 15, 2020.
Size: Uniform, medium.

*Average diameter axially.*—2½" [63.5 mm.].
*Average diameter across cheek plane.*—2½" [63.5 mm.].
*Average diameter across suture plane.*—2⅝" [66.7 mm.].
*Typical weight.*—6.1 ounces [173 grams].

Form: Uniform, fairly globose, symmetrical.

*Longitudinal section form.*—Fairly round.
*Axial view form.*—Round.

Suture: A shallow trough extending from the base to the apex.
Ventral surface: Rounded, lipped on both sides.
Lips: Fairly equal.
Cavity: Flaring.

*Depth.*—¼" [6.4 mm.].
*Breadth.*—⅞" [22.2 mm.].

Base: Truncate, cordate if viewed parallel to the suture.
Apex: Rounded.
Pistil point: An inconspicuous Moderate brown [58. m.Br] dot slightly depressed within the suture.
Stem: Medium.

*Average length.*—½" [12.7 mm.].
*Average width.*—1/16" [1.6 mm.].

Skin:

*Thickness.*—Medium.
*Surface.*—Smooth.
*Tenacity.*—Tenacious to the flesh.
*Astringency.*—Moderate.
*Tendency to crack.*—None observed.
*Color.*—Very dark purplish red [260. v.d.pR] smoothly blending into Very deep red [14. v.deep R] with very fine Pale yellow [89. p.Y] freckling throughout.

Flesh:

*Color.*—Very dark red [17. v.d.R] throughout.
*Surface of pit cavity.*—Covered with Very deep purplish red [257. v.deep pR] fibers.
*Amygdalin.*—Scarce.
*Juice.*—Abundant, rich.
*Texture.*—Firm, crisp.
*Fibers.*—Fine, tender.
*Ripens.*—Fairly even.
*Flavor.*—A very tasty blend of acid and sugar, typically 19 brix.
*Eating quality.*—Very good.
*Aroma.*—Very slight.

STONE

Type: Semi-freestone.
Form: Oval to obovate.
Hilum: Narrow.
Base: Rounded to slightly cordate.
Apex: Acuminate.
Tip: Sharp, about 1/64" [0.4 mm.] in length.
Sides: Fairly equal.
Surface: Fairly smooth with rounded ridges toward the base.
External color of stone: Light brown [57. l.Br].
Pit wall color when cracked: Moderate yellowish brown [77. m.yBr].
Cavity surface color: Light yellowish brown [76. l.yBr].
Average pit wall thickness.—1/8" [3.2 mm.].
Average length.—¾" [19.1 mm.].
Average width.—½" [12.7 mm.].
Average breadth.—⅜" [9.5 mm.].
Tendency To split: None observed.
Kernel:

*Form.*—Oval.
*Skin color.*—Moderate yellowish brown [77. m.yBr].
*Pellicle color.*—Dark yellowish brown [78. d.yBr].
*Vein color.*—Grayish yellowish brown [80. gy.yBr].
*Taste.*—Bitter.
*Viable.*—Yes.
*Average length.*—½" [12.7 mm.].
*Average width.*—⅜" [9.5 mm.].
*Amygdalin.*—Moderate.

USE

Market: Fresh market and long distance shipping.

Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, *Prunus salicina*, substantially as illustrated and described, that is most similar to its seed parent 'Blackred V' interspecific tree (U.S. Plant Pat. No. 19,576), by being self-unfruitful and by producing fruit that matures in late June and that is fairly globose in shape, firm in texture, juicy, very sweet, and very good in flavor, but is distinguished therefrom by producing fruit that is somewhat darker red in flesh color, dark purplish red instead of genetically black in skin color, larger in size, semi-freestone instead of clingstone in type, and more tolerant to high temperatures during the harvest season.

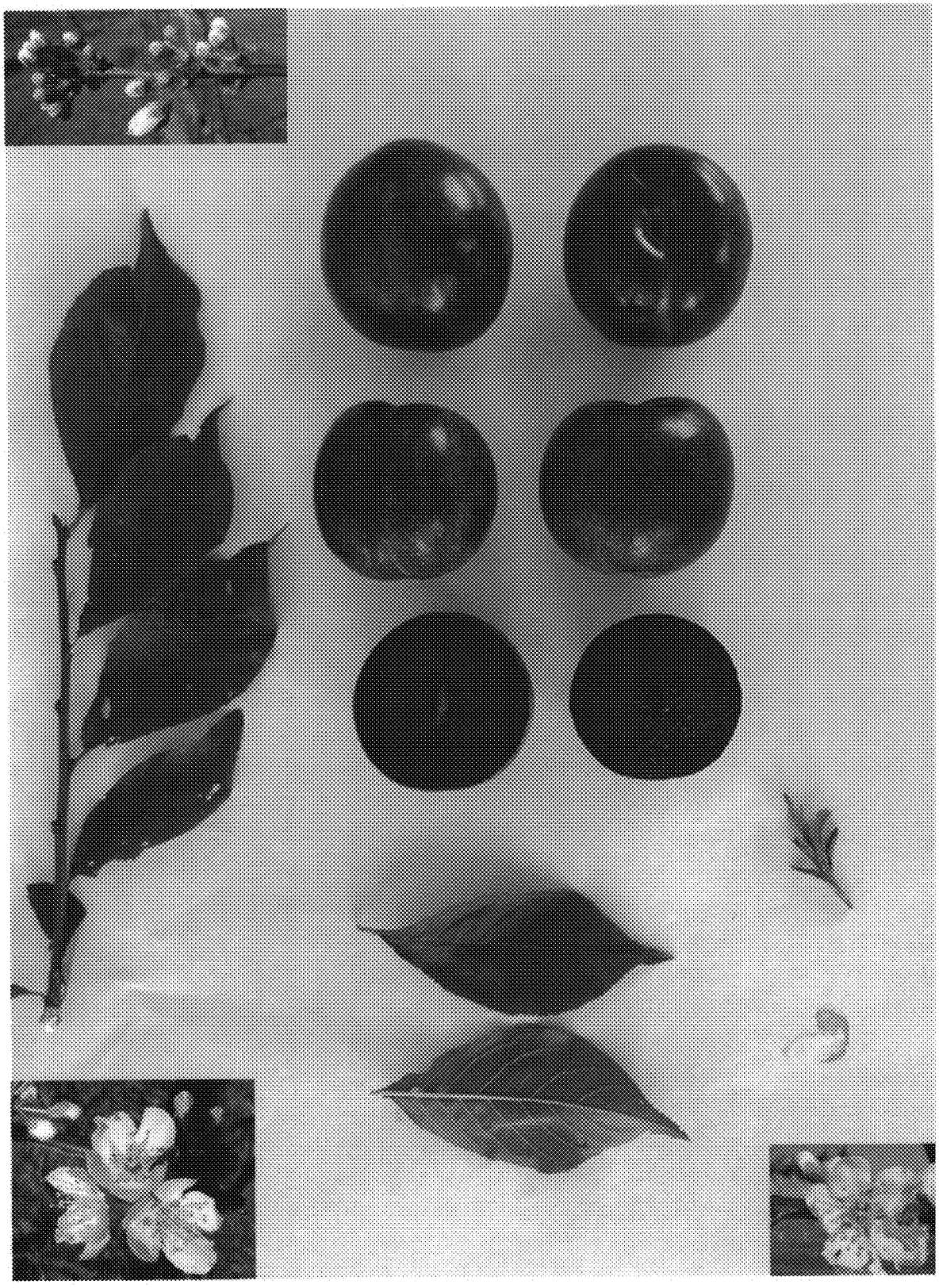

* * * * *